United States Patent [19]

Whipple et al.

[11] Patent Number: 4,662,371

[45] Date of Patent: * May 5, 1987

[54] SURGICAL INSTRUMENT

[76] Inventors: Terry L. Whipple, 8711 Standish Ln., Richmond, Va. 23229; Douglas D. Sjostrom, 17 Gladstone St., Wakefield, Mass. 01880

[*] Notice: The portion of the term of this patent subsequent to Jun. 11, 2002 has been disclaimed.

[21] Appl. No.: 743,098

[22] Filed: Jun. 10, 1985

Related U.S. Application Data

[63] Continuation of Ser. No. 461,251, Jan. 26, 1983, Pat. No. 4,522,206.

[51] Int. Cl.$^4$ .............................................. A61B 17/16
[52] U.S. Cl. .................................. 128/312; 128/305; 604/22; 604/902
[58] Field of Search ............... 128/305, 312, 751–754, 128/304; 604/48, 902, 22; 15/421

[56] References Cited

U.S. PATENT DOCUMENTS

| | | |
|---|---|---|
| 1,493,240 | 5/1924 | Bohn . |
| 1,754,806 | 4/1930 | Stevenson . |
| 1,944,739 | 6/1934 | Hunt . |
| 2,011,169 | 8/1935 | Wappler . |
| 2,473,620 | 6/1949 | Teague, Jr. . |
| 2,601,513 | 6/1952 | Gladstone . |
| 2,691,370 | 10/1954 | Wallace . |
| 2,715,899 | 8/1955 | MacLean . |
| 2,751,908 | 6/1956 | Wallace . |
| 2,790,437 | 4/1957 | Moore ..................................... 128/2 |
| 3,561,429 | 2/1971 | Jewett . |
| 3,807,406 | 4/1974 | Rafferty et al. . |
| 3,844,272 | 10/1974 | Banko ..................................... 128/2 |
| 3,895,636 | 7/1975 | Schmidt . |
| 3,964,468 | 6/1976 | Schulz . |
| 3,980,086 | 9/1976 | Kletschka et al. . |
| 3,989,033 | 11/1976 | Halpern et al. . |
| 4,043,343 | 8/1977 | Williams . |
| 4,099,529 | 7/1978 | Peyman ..................................... 604/22 |
| 4,122,856 | 10/1978 | Mosior et al. . |
| 4,203,444 | 5/1980 | Bonnell et al. ....................... 128/305 |
| 4,243,047 | 1/1981 | Olsen ..................................... 128/751 |
| 4,274,414 | 6/1981 | Johnson et al. ...................... 128/305 |
| 4,282,884 | 8/1981 | Boebel . |
| 4,369,768 | 1/1983 | Vukovic . |
| 4,369,788 | 1/1983 | Goald ..................................... 128/751 |
| 4,400,168 | 8/1983 | Buuchel ................................. 604/48 |

FOREIGN PATENT DOCUMENTS

| | | |
|---|---|---|
| 245402 | 4/1911 | Fed. Rep. of Germany ...... 128/305 |
| 1117258 | 11/1961 | Fed. Rep. of Germany . |
| 536059 | 4/1922 | France . |
| 1451726 | 7/1966 | France ................................. 128/752 |
| 2479680 | 10/1981 | France . |
| 2042902 | 10/1980 | United Kingdom . |
| 146433 | of 1962 | U.S.S.R. . |

OTHER PUBLICATIONS

"Acuflex" Linear Basket Forceps, (no date).
Omega Medical Systems, Inc. "Arthroscopic Suction Cutter", McFarland, M.D., Mar. 1981.
"Operating Instruments for Arthroscopy", Karl Storz (no date).
Stryker Corporation Arthroscopic Instruments, (no date).
"Arthroscope", Wolf, pp. B20a,B29–B29a, (no date).

*Primary Examiner*—Stephen C. Pellegrino
*Assistant Examiner*—Gene B. Kartchner

[57] ABSTRACT

Cutting-suctioning instrument having an elongated support and first and second, opposed distal jaws, at least one of which is pivotable about a transverse axis and adapted to be closed by an actuator, and a suction throat defined between proximal portions of the two jaws. Preferably, a sliding inner tube, which defines the suction passage, serves as actuator to move the pivotable jaw. As a cutter for meniscal cartilage, a hollow tube defining a tissue-fragment transport, suction passage is arranged to communicate through the open throat with the region between the jaws to receive cut tissue while suction is associated with the proximal end of the instrument for enabling tissue to be drawn from between the jaws, through the throat and thence through the transport passage while the instrument remains in situ for repeated cutting. Preferred embodiments of the instrument are especially useful in arthroscopic surgery.

5 Claims, 14 Drawing Figures

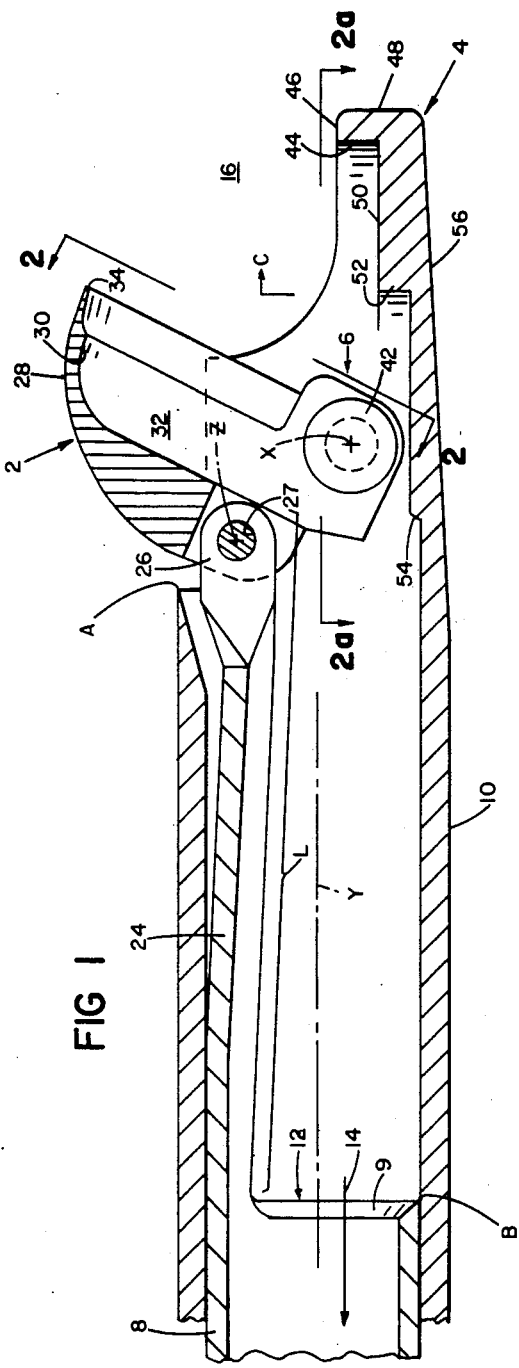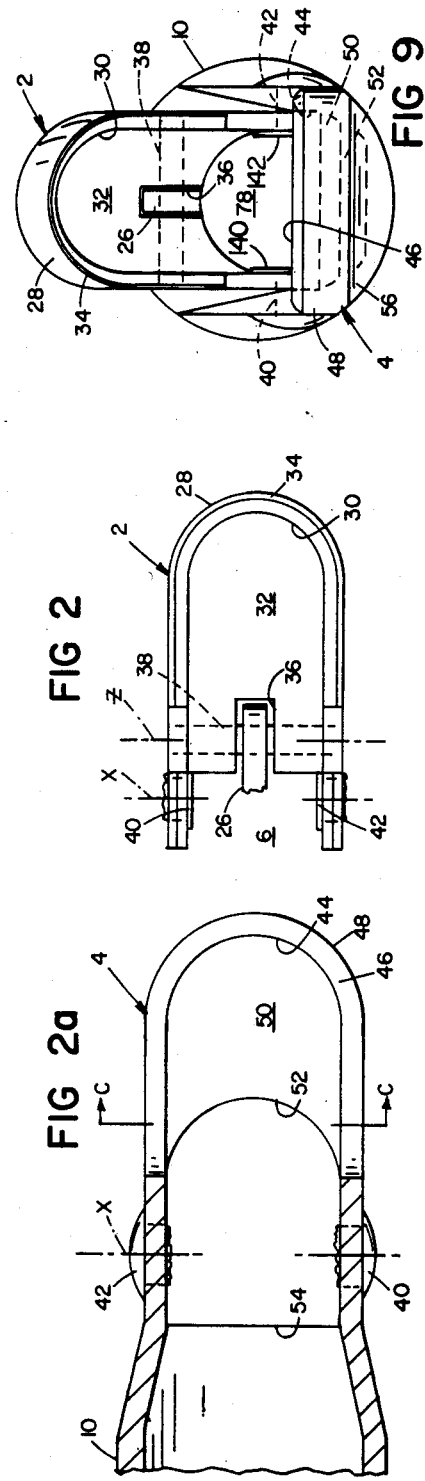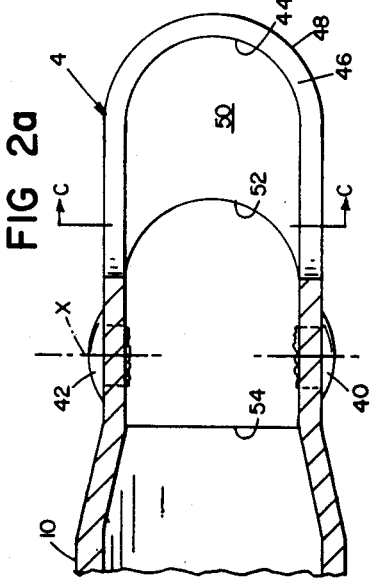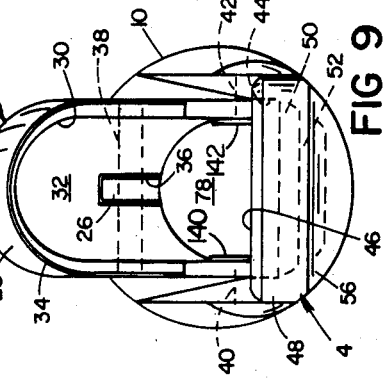

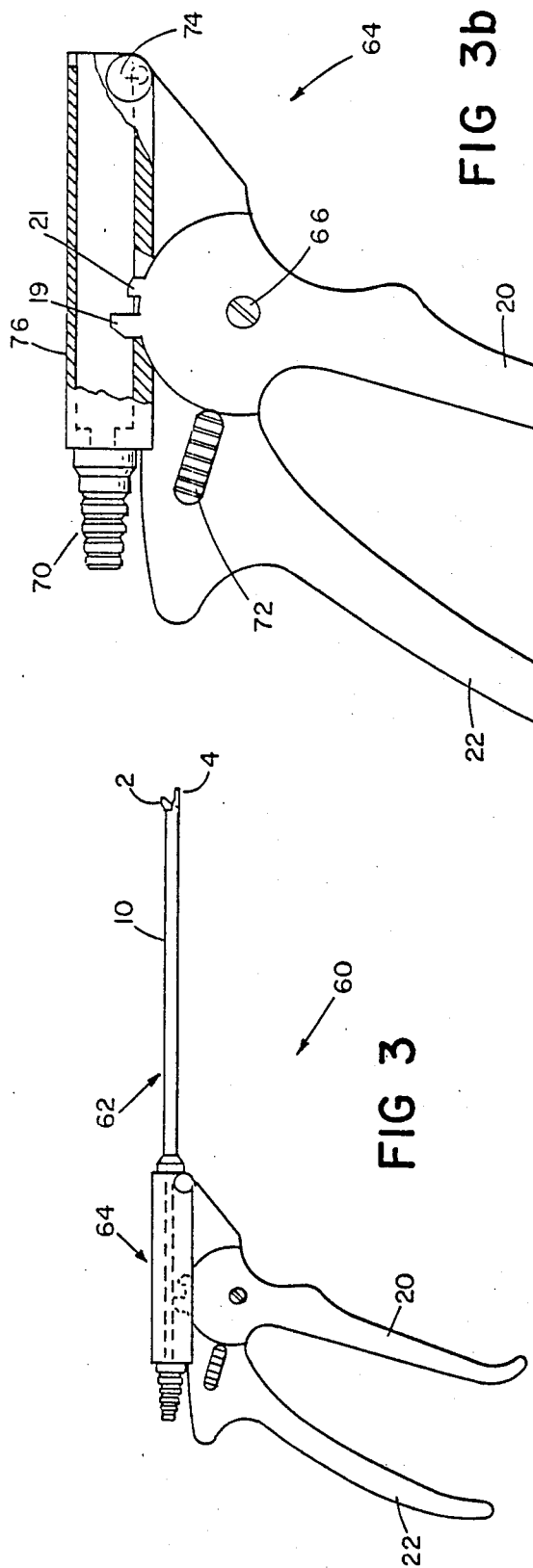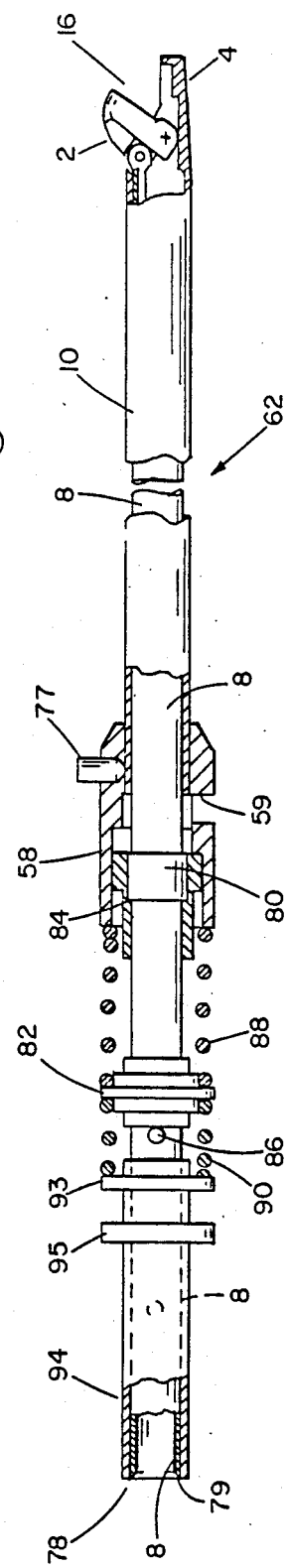

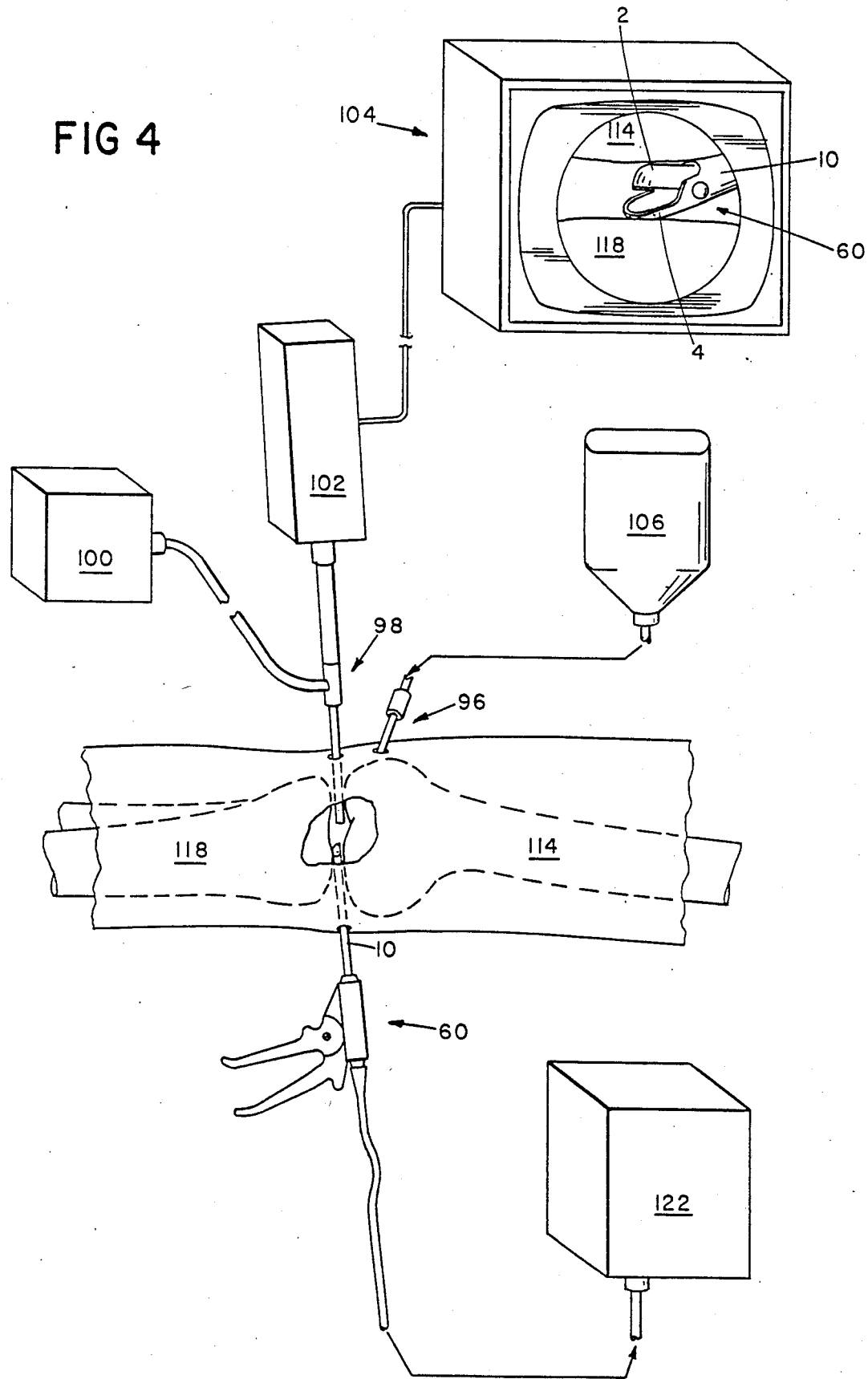

SURGICAL INSTRUMENT

This is a continuation of application Ser. No. 461,251 filed Jan. 26, 1983 now U.S. Pat. No. 4,522, 206.

This invention relates to surgical instruments for cutting fragments of tissue from an operative site and the like. The invention has particular application to arthroscopic surgery of the knee.

During use of conventional surgical forceps, after cutting a fragment of tissue, the surgeon ordinarily moves the forceps to a place away from the operative site to release the fragment, or releases the fragment at the site, for later removal. Each involves a disadvantage, i.e. extra motion and loss of time or an obscured view of the operative site.

In the case of arthroscopic surgery such as of the knee, these disadvantages are heightened. In this case the forceps enter the liquid-filled knee capsule through a puncture in the flesh, usually through a cannula placed in the puncture. It is distracting and time-consuming to the surgeon to remove the instrument from the puncture, release the fragment on the outside and then guide the instrument back into the knee to find its place for the next cut. On the other hand, if the severed fragment is released within the knee capsule, it becomes a free floating body that can occlude arthroscopic vision and pose the danger of being left to interfere with action of the joint following surgery.

Powered instruments offered by Dyonics, Inc., have to a substantial degree met these problems, but such instruments require a change of technique from that of the hand-actuated instruments with which surgeons are most familiar, and have, in certain ways, some other disadvantages.

Objects of the invention are to overcome these difficulties with a durable and simple hand-actuated instrument.

Summary of the Invention

According to one aspect of the invention, a surgical instrument is specially constructed to have an open throat between proximal portions of distal jaws constructed and arranged, when open, to provide a distally-directed, end aperture through which tissue can enter. The jaws pivot relatively to one another on an axis transverse to the axis of their proximal support. This support is constructed to provide an open, tissue fragment transport, suction passage through its length, and suction means are associated with the proximal end of the fragment transport passage. By this arrangement, upon opening of the jaws of the instrument, differential fluid pressure acts endwise through the opened jaws, the open throat and the fragment transport passage, to draw the tissue fragment cut by closing action of the jaws and transport it through and out of the instrument. The fragment can thus be removed from the surgical site while the instrument remains in situ to be opened and closed in further cutting and removal cycles. Instruments of such construction can also be employed as suction graspers, e.g. for grasping or maneuvering free bodies that are too large for passage through the instrument.

In an instrument suitable for arthroscopic surgery in a joint such as the knee, the jaws and their support are sized to enter the joint through a puncture in the flesh and to be manipulated under arthroscopic guidance.

In preferred embodiments: the jaws of the instrument define mating U-form cutting edges, preferably one jaw being fixed and the other being movable, with the movable jaw having a slightly smaller form, sized to enter the space defined by the edge of the fixed jaw during closing action of the instrument; the support for the jaws comprises an elongated outer hollow member, a lower distal extension of which defines the fixed jaw, and the open throat is defined between a proximal portion of the movable jaw and the adjacent side of this hollow member; the actuator for the movable jaw is in the form of an inner hollow tube adapted to be moved axially relatively to its support, an integral axial extension of this inner tube being adapted to bend resiliently relative to the axis of the instrument during the axial motion to actuate the movable jaw in its cutting action, this inner hollow tube providing the tissue fragment transport, suction passage, preferably this inner tube being slidably supported by a stationary outer tube.

In another aspect, the invention comprises a surgical instrument comprising inner and outer coaxial hollow tubes, the outer tube serving as a support and having a distal extension defining a fixed jaw, the inner tube being axially slidable within the outer tube and being associated at its distal end with a jaw pivotable about an axis disposed generally transversely to the axis of the support, the pivotable jaw being shaped to move against the fixed jaw in response to axial movement of the hollow inner tube, the hollow inner tube being arranged to communicate with the region between the jaws, and suction means associated with the proximal end of the inner tube for applying suction between the jaws, there also being hand-operable means, e.g. a handle and lever, to enable the operator of the instrument to move the inner tube to actuate the movable jaw.

Furthermore, in preferred embodiments, the flow cross sectional area of the suction passage is of the order of one third or more of the cross sectional area of the outer tube and the minimum cross sectional area in the region of the jaws is of the order of one half or more of the flow cross section of the suction passage; the movable jaw has lateral sides pivotally mounted on a support axis by stub pins to corresponding sides of the outer hollow member, the open throat having a width that corresponds substantially to the spacing between the inner surfaces of the sides of the pivotable jaw; the pivotable jaw has an actuating crank, and an elongated push/pull actuating member is pivotally connected to this crank at a moving pivot point that swings about the pivot axis; the minimum vertical dimension of the open throat is defined between one side of the suction passage in the region of the moving pivot; in closed position the moving pivot lies distally of the transverse pivot axis of the pivotable jaw, and as this jaw is opened from its closed position by the push/pull member, the moving pivot is constrained to swing proximally and outwardly about the transverse pivot axis, thereby to open the throat wider and facilitate movement of severed tissue fragments; preferably this push/pull actuating member lies along one side of the transport suction passage, and is able to resiliently flex outwardly as the moving jaw moves open from its closed position to increase the size of the respective region of the passage, preferably the push/pull member comprises an elongated, distal extension of an inner hollow tube, this hollow tube defining a proximal portion of the passage and being axially slidable relative to the elongated support to activate the movable jaw; the movable jaw is actuated by a lever that extends at a significant angle to the axis of the support, preferably the lever being operable at angles in the range of about 100° to about 135° relative to the axis; the instrument further comprise means adapted to bypass the path of suction from the suction means, and means for selectively deactivating this means to cause a fluid pressure differential to act through the distal end of the instrument, and for activating the suction by-pass means to substantially reduce the fluid pressure differential acting through the distal end of the instrument, preferably the suction by-pass means comprising at least one port defined through the wall of the suction passage, and the means for selectively activating and deactivating the suction by-pass means comprises a sleeve moveably positioned about the wall, and the sleeve is positioned relative to the ports by the selective position of the jaw actuator; the cutting interaction of the jaws occurs on a pivot axis transverse to the axis of the support; and the suction connection means associated with the proximal end of the transport, suction passage is adapted for continuous suction through said passage.

According to still another aspect of the invention, the movable jaw is pivotally mounted at a pivot axis at a position near one side of the transport, suction passage, a crank associated with this movable jaw has a moving pivot point positioned to move generally axially in the region of the opposite side of the passage, and the push-/pull actuator, preferably in the form of the aforementioned resilient extension of the inner tube, extends distally along the opposite side of the passage to a connection with this moving pivot.

According to other aspects of the invention, an instrument has an axially elongated support for distal jaws of the aforementioned structure.

PREFERRED EMBODIMENT

The structure and operation of a preferred embodiment of the invention will now be described, after first briefly describing the drawings.

DRAWINGS

FIG. 1 is a side view of the preferred embodiment of the instrument at rest with the jaws open;

FIGS. 2 and 2a are plan views of the fixed and movable jaws of FIG. 1, respectively;

FIG. 3 is a plan view of the instrument, while FIGS. 3a and 3b are plan views of the blade and handle portion, respectively, of the instrument;

FIG. 4 is a diagrammatic view showing the set-up of the instrument according to the invention with typical accessories for performing intra-articular surgery of the knee;

FIG. 9 is an end view of the instrument with the jaws open in the position of FIGS. 6 or 8, illustrating the throat opening and the through flow of the instrument.

STRUCTURE OF THE INSTRUMENT

Figure 5:
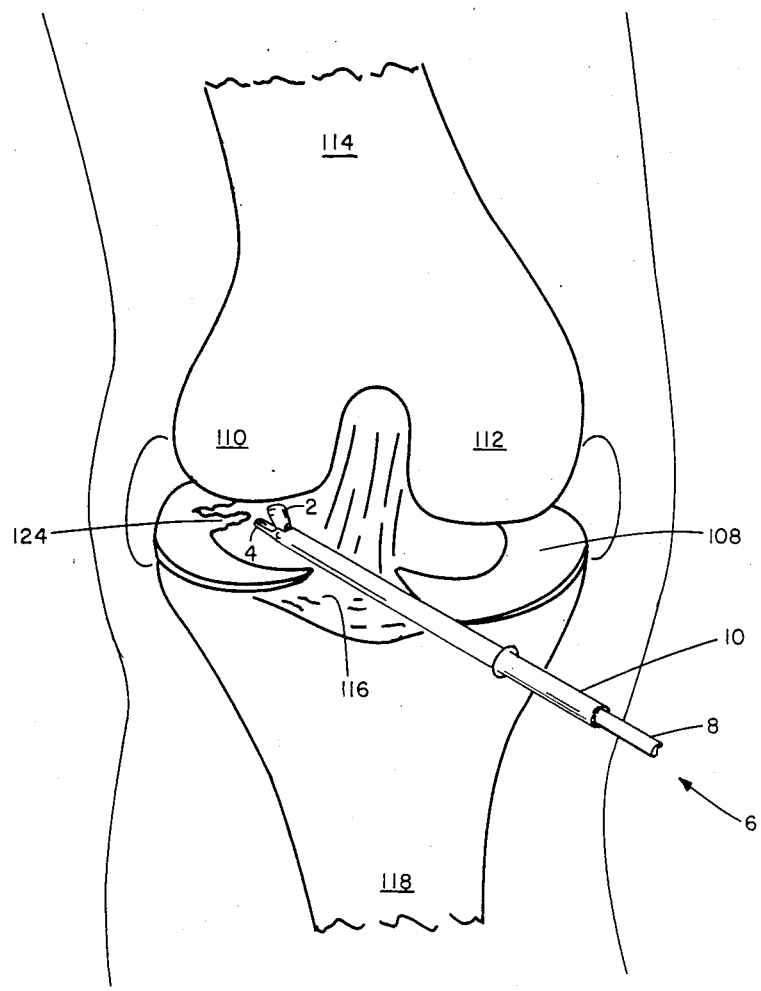
FIG. 5 is a representation of the knee with the instrument of FIG. 3 being inserted into the joint.

Referring generally to FIG. 1, distal jaws 2 and 4, respectively, of a surgical instrument are specially constructed to provide a proximal open throat 6 between the jaws, actuating member 8 being provided to operate jaws 2, 4 to cooperatively cut a segment of tissue and proximal support 10 for the jaws being constructed to provide an open, tissue fragment transport, suction passage 12 extending through the length of the support. Suction means denoted by arrow 14 is associated with the proximal end of this passage.

Upon opening of the jaws after a fragment of tissue has been cut, differential fluid pressure acts at 16 through the open jaws 2, 4, the open throat 6, and the fragment transport passage 12 to cause the tissue fragment 18 (FIGS. 6–8) to be dislodged from the jaws and transported through throat 6 and fragment transport passage 12 and out of the instrument.

Movable upper jaw 2 is pivotally mounted, at X, to outer support tube 10 to rotate against fixed lower jaw 4 which constitutes an extension of the outer tube. The actuating member 8 is an inner tube which is caused to reciprocate by squeezing action of the surgeon on the actuating lever 20 against the handle 22 (FIG. 3).

Referring more specifically now to FIGS. 1, 2 and 2a, in the preferred embodiment of the instrument, the outer support comprises an outer hollow tube 10, the lower extension of which comprises fixed jaw 4. The upper portion of hollow outer support tube 10 terminates at A, which lies proximally of the distal end of fixed jaw 4. Moveable jaw 2 is pivoted about axis X, which lies below the center axis Y of the outer support tube 10, and in a plane perpendicular to axis Y.

The actuating member comprises an inner hollow tube 8, which over its major length, to B, defines tissue fragment transport, suction passage 12. The major portion of the circumference of inner tube 8 is terminated at B, proximally of the distal termination of outer support tube 10, and the end surface 9 is beveled inwardly at the termination to facilitate flow of severed tissue fragments into passage 12. The distally extending portion of inner tube 8 comprises elongated tang 24 which is flexible axially over length, L. The distal end 26 of tang 24 is formed for hinged connection, at axis Z, also in a plane perpendicular to axis Y, to moveable jaw 2.

Referring to FIG. 2, moveable jaw 2 viewed from within the bite has U-shaped outer surface 28 and an inner surface 30 which defines an open cavity 32 surrounded distally on three sides by jaw lip 34. At the proximal end, cavity 32 opens into throat 6. At the upper proximal surface of moveable jaw 2, end 26 of tang 24 is received into slot 36. Hinge pin 38, shown in dashed line in FIG. 2, lying along hinge axis Z, parallel to axis X, passes through the body of jaw 2 at either side of slot 36 and through hole 27 in the end portion of tang 24 to form a hinged connection between moveable jaw 2 and actuating means 8.

Moveable jaw 2 is pivotally connected to hollow outer support tube 10 by stub pins 40, 42 on axis X, transverse to and below the center axis Y. Stub shafts 40, 42 extend through the side walls of outer tube 10 distal to point A and through the lower proximal side surfaces of moveable jaw 2 at either side of throat 6.

Referring now to FIG. 2a, fixed jaw 4 has a similar U-shape, with inner surface 44 sized and configured to receive the outer surface 28 of moveable jaw 2 in a close sealing relationship. The top surface 46 of fixed jaw lip 48 is "chased", i.e. burnished, inwardly about 0.001 inch up to 0.005 inch, starting at C on both sides of jaw 4 and extending about the distal end, to ensure close tolerance between jaw lips 34, 48 for clean cutting action between the jaws. The distal inner surface of fixed jaw 4, i.e. floor 50, is relieved in two steps 52, 54 (FIG. 1) moving proximally through throat 6 toward tissue fragment transport passage 12. The outer surface 56 of fixed jaw 4 flattens and tapers upwardly toward center axis Y approaching the distal end of the instrument to facilitate positioning the cutting jaws during surgery, as further discussed below.

Referring to FIGS. 3, 3a land 3b, the instrument portion that remains external of the patient's body will now be described in relation to the operative instrument portion already described.

In FIG. 3, instrument 60 is shown in assembled form.

In FIG. 3a, the blade portion 62 of instrument 60 is shown. Outer support tube 10 extends into blade retention sleeve 58. Sleeve 58 has notch 59 in its lower surface for attachment to the instrument handle 64 shown in FIG. 3b.

Instrument handle 64 comprises fixed handle 22 upon which, at 66, is pivotally fixed a trigger or actuating lever 20. Handle 64 further comprises suction fitting 70 located at the proximal end of the instrument for connection of the tissue fragment transport passage 12 to the hospital vacuum system. Trigger latch 72 is configured to engage trigger 20 to fix the jaws at selected positions, e.g. full closed, to allow the surgeon to position or reposition the instrument without having to maintain pressure on the trigger. The shaft of blade lock screw 74 in a first position engages in notch 59 of sleeve 58 to retain the blade portion 62, shown in FIG. 3a, within the body. In a second position, screw 74 disengages from notch 59 to allow the blade portion to be removed from the body by movement along the support axis Y. Cover 76 has a notch (not shown) to receive pin 77 extending from sleeve 58 for proper radial alignment of blade portion 62 assembly in instrument handle 64. Cover 76 encloses the actuating portion of the instrument, as now more fully described with reference again to FIG. 3a.

Outer support tube 10 terminates within sleeve 58. Inner tube 8, defining the tissue-fragment transport passage 12, extends to the proximal end 78 of blade portion 62. Permantly fixed about inner tube 8 are stop sleeve 80 and front actuating sleeve 82. Stop sleeve 80 limits the axial range of movement of tube 8 between positions of abutment with the retention sleeve 58 in the distal, i.e. closing, direction and jaw opening stop 84 in the proximal, i.e. opening, direction. Jaw opening stop 84 is positioned within the aperture provided at the proximal end of retention sleeve 58 to allow the moveable jaw 2 to open only to within about 5% of maximum to prevent stress on the instrument parts within the knee during the opening stroke. The stop sleeve is similarly positioned to prevent damage on the cutting stroke.

Suction by-pass holes 86 pass through the wall of inner tube 8 at 90° to each other into tissue-fragment transport passage 12 to allow selective reduction of the differential fluid pressure acting through the open jaws at 16, as discussed more fully below.

Main spring 88 between retention sleeve 58 fixed to outer support tube 10 and front actuating sleeve 82, fixed on inner actuating tube 8, urges the inner tube 8 in the proximal direction to hold jaws 2, 4 in the open position. Secondary spring 90, between fixed front actuating sleeve 82 and rear actuating sleeve 94, axially moveable along inner tube 8, urges the sleeve 94 in a proximal direction away from sleeve 82. The movement of sleeve 94 is limited proximally by providing a flare 79 at the proximal end of tube 8.

Flanges 93, 95 extend radially from rear actuating sleeve 94 in a spaced relationship. In assembled form (FIG. 3), the prongs 19, 21 of trigger 20 engage either side of flange 95.

Operation of the Surgical Forceps Instrument

Referring more specifically now to FIGS. 4 and 5, in FIG. 4, the instrument 60 is shown inserted into knee joint 96. At the same time, a fiber optic device 98 introduces light to the interior of the joint from light source 100 and returns a visual image along a separate optical path. While the image can be directed to an eye piece for the surgeon, as well as to recording cameras, in the preferred embodiment shown, the image is directed to television camera 102 which creates the display 104, which the surgeon watches to control his movements. By thus watching the screen and manipulating the instrument, the surgeon positions the instrument for removal of tissue, as shown in the TV picture.

During operation, the joint is distended by providing saline fluid under controlled hydrostatic pressure from source 106.

During the operative procedure as shown in FIG. 4, the patient may be given general anesthesia and appropriate punctures of the patient's flesh are made at selected points about the joint by a trocarring cannula. Fluid is introduced from source 106 into one cannula at a slightly increased pressure to distend the joint, and to provide flow through the joint to 16 through the open jaws 2, 4 of the instrument 60. This substantial volume of flow, in excess of 100 cc per minute, is necessary to ensure that all the tissue severed from the joint is drawn into the instrument 60 through jaws 2, 4, throat 6, tissue-fragment transport passage 12 and removed from the joint; it also keeps the joint fluid clear for better visual guidance of the instrument.

Visualization instrument 98 is inserted into the joint through another cannula.

The surgeon squeezes trigger 20 toward handle 22 to close jaws 2, 4 and activates the trigger latch 72 to hold the jaws closed without pressure on the trigger. The distal end of the instrument is inserted through a third cannula into the knee joint 96 of the patient, or may e.g. with larger diameter instruments, be inserted directed through the puncture to reduce the size of the wound required. In FIG. 5, instrument 60 is shown in position for surgical removal of a portion of the meniscal cartilage 108 lying between the condyls 110, 112 of the femur (thigh bone) 114 and the end 116 of the tibia (shin bone) 118.

The instrument is critically sized for insertion into the tight confines of the knee joint, e.g. typical instruments may be about 5.2 mm or 3.4 mm diameter. The support tube also has sufficient strength to resist bending when the surgeon applies force to position the cutting end, while permitting a tissue-fragment transport passage of at least one third of the cross sectional area of the support for easy passage of severed tissue-fragments through the instrument and out of the body. To facilitate entry into the wedge-shape area between the surface of the tibia and the femoral condyles, the lower jaw 4 has a flat bottom surface 56 at the distal end and tapers upward toward the center axis Y.

Once the jaws of the instrument are positioned, as observed by the surgeon on television display 104, he squeezes trigger 20 lightly and releases trigger latch 72. Main spring 88 acts against front actuating sleeve 82 to move actuating means, i.e. inner tube, 8 proximally which in turn causes the hinge connection, axis Z, to rotate proximally about pivot X, causing jaws 2 to open. Secondary spring 90 between front actuating sleeve 82 and rear actuating sleeve 94 urges sleeve 94 proximally to abut with the flanged end of inner tube 8. This movement of sleeve 94 exposes suction by-pass ports 86 causing the suction drawn through suction fitting 70 to by-pass, and substantially no pressure differential is generated through the open jaws at 16. This feature reduces the amount of fluid that must be supplied into the knee from source 106 by allowing the surgeon to substantially reduce flow when desired. It also provides the ability to create a surging effect within the tissue-fragment transport passage 12, if desired, by rapidly squeezing and unsqueezing trigger 20 to alternately cover and expose ports 86, e.g. to dislodge any fragments clogged in the tube.

To begin the procedure, the surgeon squeezes trigger 20 toward handle 22 lightly. This causes trigger prong 19 against flange 95 to urge rear sleeve 94 distally against secondary spring 90 until ports 86 are covered. Main spring 88 and secondary spring 90 are cooperatively sized so rear sleeve 94 closes ports 86 and abuts front actuating sleeve 82 before there is any substantial movement of sleeve 82 against spring 88 to close jaws 2, 4.

At this point, the entire pressure differential generated by suction source 122 (typical hospital vacuum is about 15 to 18 inches of mercury) is present at 16 to draw fluid provided from source 106 through jaws 2, 4, throat 6, tissue-fragment transport passage 12, and out of the body.

The volume of fluid introduced into the joint from the fluid source 106 is balanced so that the same volume is removed through the instrument, with the inflow maintained at slightly higher pressure, typically at about 1 to 1.5 meters of head, to appropriately distend the joint.

Figure 6:
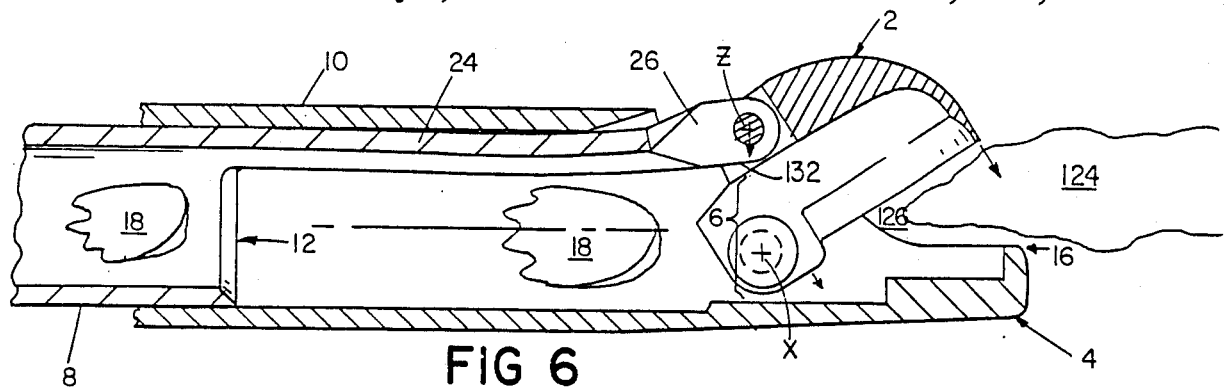
FIGS. 6 through 8 are side views in section showing a cutting and fragment removal cycle, with discrete fragments of tissue being removed through the instrument.

Referring now to FIGS. 6, 7, 8 and 9, a cutting and removing sequence will be described. In FIG. 6, the surgeon is holding trigger 20 to generate pressure differential at 16 through the jaws, with portions of the actuating means and moveable jaw poised to move in the directions shown by the arrows. The hinge axis Z and pivot axis X are aligned in a plane perpendicular to support axis Y. At this point, tang 24 is flexed slightly outward from center axis Y to accommodate the radius of axis Z about axis X. This, in turn, increases the area of throat 6 to its maximum, typically one third or more of the flow area of the fragment transport passage 12, to enable ready movement of the fragment. The surgeon, observing through the arthroscope or the TV monitor, positions the distal bite 126 the instrument about a section of tissue 124 to be removed.

Figure 7:
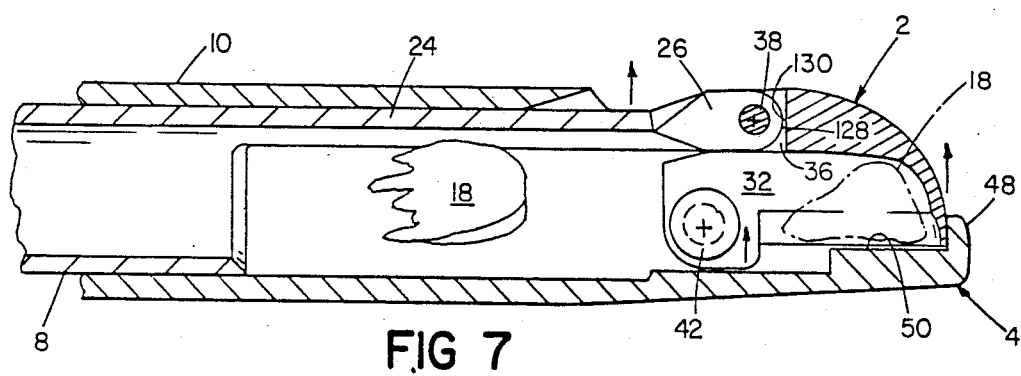

In FIG. 7, the surgeon has squeezed the trigger to close the jaws and sever the tissue fragment 18 now held in cavity 32 formed by moveable jaw 2 above the floor 50 of fixed jaw 4. The cross sectional area of cavity 32 containing the tissue fragment is typically less than the cross sectional area of throat 6 to size the fragment for easier flow through the constriction. A clean cut is achieved due to the close tolerance cutting edge provided on the lower jaw lip 48 by the burnishing which loads the interaction, and due to the close-fitting relationship of the outer surface 28 of jaw 2 and the inner surface 44 of jaw 4. An interaction is also provided between the distal surface 128 of tang end 26 and the distal surface 130 of slot 36 to ensure a close tolerance fit between the jaw lips, even if, e.g., wear occurs on hinge pin 38 or stub shafts 40, 42.

Figure 8:
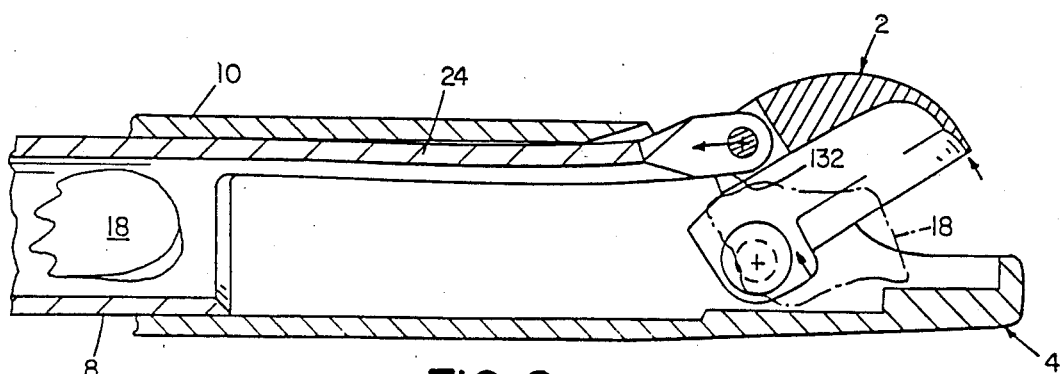

In FIG. 8, the jaws have been returned to the position shown in FIG. 6. As the jaws open, suction through the opening draws the severed tissue fragment 18 toward throat 6. As shown in FIG. 9, throat 6 is a constriction in the flow passage of the tissue fragment, as the head 140, 142 of stub pins or shafts 40, 42, respectively, protrude into the passage. However, as axis Z rotates to the position shown in FIG. 8, the area of throat 6 is enlarged by the outward flexing of tang 24 to ease passage of the severed tissue therethrough. This also corresponds to the maximum fluid flow through the passage as the point of maximum constriction, i.e. throat 6, is at its maximum flow area. The differential pressure across the instrument draws the tissue fragment out of the jaws, through the throat and tissue-fragment transport passage 12, out of the instrument and out of the body. As seen in FIG. 9, the instrument provides a straight flow-through passage for the severed tissue, with the opening at the proximal end 78 of the instrument visible through the jaws. Thus the severed tissue is removed from the knee joint out of the body while the instrument remains in situ within the joint ready for the next cut.

If a tissue fragment becomes lodged in the throat area, throat point 132 is provided at the upper proximal surface of moveable jaw 2. Rapid open and closing of jaws 2, 4 by squeezing and releasing trigger 20 causes a "ratcheting" motion of throat point 132 about axis Z on the lodged tissue fragment urging it proximally out of the throat, in cooperation with the suction flow, during the closing motion. (During the opening motion, the suction flow continues to urge the fragment proximally while the motion of the distal surface of point 132 sliding on the fragment surface does not apply significant force in the distal direction.)

Furthermore, during the opening motion shown in FIG. 8, tang 24 and tang end 26 in throat 6 move axially to apply force in the proximal direction which, in cooperation with the suction flow through the instrument, further cause the tissue fragment 18 to pass through throat 6 and toward fragment transport passage 12. (During the closing motion (FIG. 6), force on tissue fragment 18 in the distal direction caused by movement of tang 24 is offset by suction flow.)

Also, if the jaws become jammed in the closed position, e.g. due to fibrous tissue in the area between the jaw surfaces 28, 44, the surgeon may force the jaws open without removing the instrument from the body by applying force to the trigger toward the distal end of the instrument. This causes trigger prong 21 to urge flange 95, and, in turn, inner actuating tube 8, proximally to open jaws 2, 4.

Other Embodiments

Figure 10:
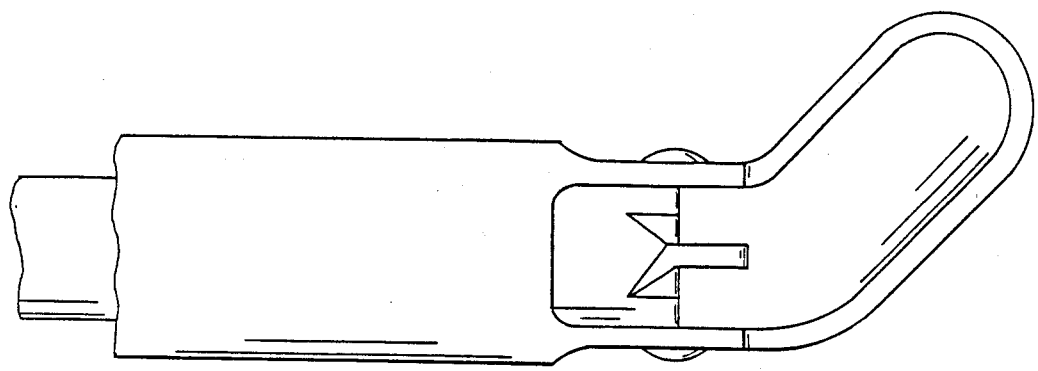
FIGS. 10 and 11 are a top view and side view, respectively, showing different alternate embodiments of fixed jaw alignment.
Figure 11:
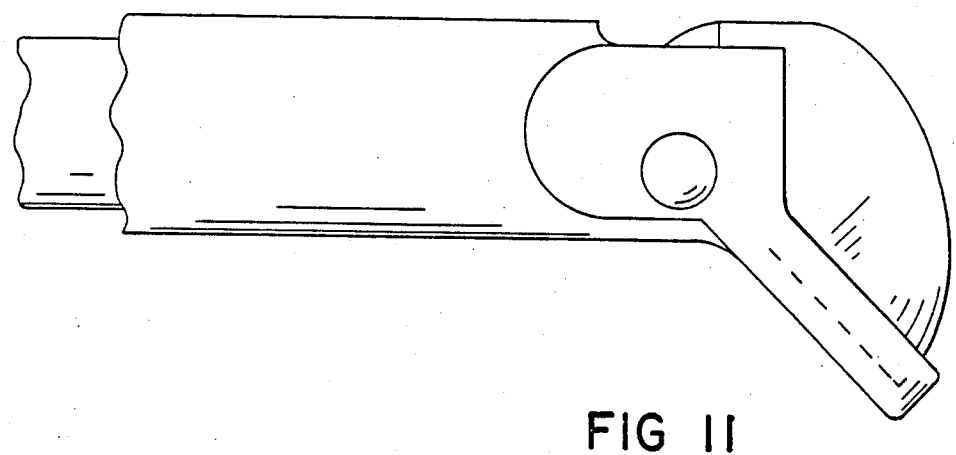

Other embodiments of the invention are within certain of the following claims. For example, the instrument may be used to perform open surgery, or with certain type of tissue may be used without liquid flow. The actuating means may be a solid rod, typically extending through the support tube close to the inner surface, as the support tube defines the tissue fragment transfer passage, or the instrument may be powered, e.g. by use of a crank on a motor, a wobble plate, or other means of converting rotational motion-to-axial motion. The inner surface of the fixed jaw may be sloped downward through the throat. The jaw configuration may be provided at any desired angle of rotation, and the bite may be provided at an angle to the center axis, e.g. at an oblique (right or left) angle, as in FIG. 10, or with the fixed jaw slanted upwardly or downwardly, as in FIG. 11. Also, means, e.g. a shear pin, may be provided in the handle portion or in the blade portion to limit the cutting pressure that might be applied to the jaws and reduce the possibility of damage to in vivo portions of the instrument, and both jaws may be rotatable relative to the support axis. Finally, other jaw configurations may be utilized, or the instrument may be used as a suctioning, grasping instrument, e.g. with longer and stronger jaws, to retrieve from the joint free floating bodies that are too large or too hard to be removed through the instrument.

We claim:

1. A surgical instrument suitable for cutting body tissue, comprising an axially elongated support, at the distal end thereof, first and second, opposed cutting jaws, said jaws having respective extending cutting edges arranged to move at least relatively toward and closely past one another in tissue-severing shearing motion, said first jaw and said second jaw, when open, being disposed on axes lying at angles transverse to the axis of said elongated support, said jaws thereby constructed and arranged to provide a generally distal end aperture through which tissue can enter, and said jaws closeable by an actuator to cut tissue extending through said end aperture into the space between said distal jaws, the movement of said jaws relatively toward one another occurring in a plane disposed transverse to the axis of said support, the cutting interaction of said jaws thereby occurring on an axis transverse to the axis of said support, said jaws being cooperatively constructed to provide an open, tissue fragment transmitting throat between proximal portions of said opposed jaws, said elongated support defining an open, tissue fragment transport, suction passage communicating with said throat and extending through the length of said support, and a suction line connector associated with the proximal end of said fragment transport passage for enabling tissue fragment removal through said passage under the influence of suction applied through said connector, said jaws and throat constructed and arranged so that fluid differential pressure acting through the distal end of said instrument and through said throat and transport passage causes a fragment of tissue cut by said jaw-closing action to be drawn proximally from between said jaws, through said open throat and fragment transport passage, and out of said instrument via said connector, whereby said fragment can be removed while said instrument can remain in situ for repeated cutting cycles.

2. A surgical instrument suitable for cutting body tissue including cartilagenous tissue and the like, comprising an axially elongated support, at the distal end thereof, first and second, opposed cutting jaws, said jaws having respective extended cutting edges arranged to move relatively toward and closely past one another in tissue-severing shearing motion, said jaws being constructed to withstand substantial cutting forces, said first jaw and said second jaw, when open, being disposed on axes lying at angles transverse to the axis of said elongated support, said jaws thereby constructed and arranged to provide a generally distal end aperture through which tissue can enter, and said jaws closable by an actuator to cut tissue extending through said end aperture into the space between said distal jaws, the movement of said jaws relatively toward one another occurring in a plane disposed transverse to the axis of said support, the cutting interaction of said jaws thereby occurring on an axis transverse to the axis of said support, said jaws being cooperatively constructed to provide an open, tissue fragment transmitting throat between proximal portions of said opposed jaws, said elongated support defining an open, tissue fragment transport, suction passage communicating with said throat and extending through the length of said support, and a suction line connector associated with the proximal end of said fragment transport passage for enabling tissue fragment removal through said passage under the influence of suction applied through said connector, said jaws and throat constructed and arranged so that fluid differential pressure acting through the distal end of said instrument and through said throat and transport passage causes a fragment of tissue cut by said jaw-closing action to be drawn proximally from between said jaws, through said open throat and fragment transport passage, and out of said instrument via said connector, whereby said fragment can be removed while said instrument can remain in situ for repeated cutting cycles.

3. A surgical instrument suitable for cutting a range of body tissue including cartilagenous tissue and the like, comprising an axially elongated support, at the distal end thereof, first and second, opposed cutting jaws, said first jaw being fixed and the second said jaw being pivotable, said jaws having respective extended cutting edges arranged to move relatively toward and closely past one another in tissue-severing motion, said jaws being constructed to withstand substantial cutting forces, said jaws constructed and arranged, when open, to provide a distal end aperture through which tissue can enter, and said jaws closable by an actuator to cut tissue extending through said end aperture into the space between said distal jaws, said jaws being cooperatively constructed to provide an open, tissue fragment transmitting throat between proximal portions of said fixed and movable jaws, said elongated support defining an open, tissue fragment transport, suction passage communicating with said throat and extending through the length of said support, said actuator comprising a rod extending through said elongated support defining said passage, and a suction line connector associated with the proximal end of said fragment transport passage for enabling tissue fragment removal through said passage under the influence of suction applied through said connector, said jaws and throat constructed and arranged so that fluid differential pressure acting through the distal end of said instrument and through said throat and transport passage causes a fragment of tissue cut by said jaw-closing action to be drawn proximally from between said jaws, through said open throat and fragment transport passage, and out of said instrument via said connector, whereby said fragment can be removed while said instrument can remain in situ for repeated cutting cycles.

4. The surgical instrument of claim 3 including means for powering movement of said jaws.

5. The surgical instrument of claim 1 or 2 further comprising means for powering movement of said opposed cutting jaws.

* * * * *

UNITED STATES PATENT AND TRADEMARK OFFICE
CERTIFICATE OF CORRECTION

PATENT NO. : 4,662,371
DATED : May 5, 1987
INVENTOR(S) : Terry L. Whipple et al.

It is certified that error appears in the above-identified patent and that said Letters Patent are hereby corrected as shown below:

Column 5, line 13, "and" is misspelled.

Column 8, line 12, "head" should be --heads--.

Column 8, line 64, "type" should be --types--.

Signed and Sealed this

Twenty-second Day of September, 1987

Attest:

DONALD J. QUIGG

*Attesting Officer*  *Commissioner of Patents and Trademarks*